United States Patent [19]

Curtiss, III et al.

[11] Patent Number: 5,424,065
[45] Date of Patent: Jun. 13, 1995

[54] VACCINES CONTAINING AVIRULENT PHOP-TYPE MICROORGANISMS

[75] Inventors: Roy Curtiss, III; Jorge Galan, both of St. Louis, Mo.

[73] Assignee: Washington University, St. Louis, Mo.

[21] Appl. No.: 981,935

[22] Filed: Nov. 19, 1992

Related U.S. Application Data

[63] Continuation of Ser. No. 331,979, Mar. 31, 1989.

[51] Int. Cl.$^6$ .......................... A61K 39/02; C12N 1/21
[52] U.S. Cl. .................. 424/93.2; 424/93.48; 424/184.1; 435/252.3; 435/252.8; 435/69.1; 435/71.1
[58] Field of Search ............. 424/88, 92, 184.1, 258.1, 424/93.1, 93.2, 93.48; 435/252.3, 69.1, 71.1, 71.2, 245, 252.8

[56] References Cited

U.S. PATENT DOCUMENTS 4,837,151  6/1989  Stocker ............................ 435/172.3

OTHER PUBLICATIONS

Fields et al Science Feb. 1989 pp. 1059–1062 vol. 243.
Curtiss et al Inf & Im. 155:3035–3043 Dec. 1987.
Nakayama et al Biotechnology vol. 6 Jun. 1988, 693–697.
Kier et al J of Bact 130:420–428 1977, Regulation of Two Phosphatases & a Cyclic Phosphodiesterase of *S. typh.*
Foster et al J of Bact 166:666–669–Phosphate Starvation Regulon of *Salmonella typhimurium.*
Germanier, R., (ed.), "Bacterial Vaccines" published 1984 by Academic Press (New York) pp. 137–165.
Brown, A., et al., *Journal of Infectious Disease* (1987) 155(1): 86–92.
Groisman et al., Proc. Natl. Acad. Sci. (1989) 86:7077–7081.
Foster et al., J. Bacteriol. (1990) 172(2):771–778.
Galan et al., Microbiol. Pathogenesis (1989) 6:433–443.
Nakayama et al Biotechnology 6:693–697 1988.
Finlay et al Molecular Microbiology 2:757–766, 1988.
O'Callaghan et al Inf & Immun 56:419–423 1988.
Hackett Vaccine 8:5–11 1990.

*Primary Examiner*—Hazel F. Sidberry
*Attorney, Agent, or Firm*—Rogers, Howell & Haferkamp

[57] ABSTRACT

The phoP gene and its equivalents are of a type which have "global regulation of pathogenicity", i.e., they coordinately regulate a number of genes including those that encode bacterial virulence factors. In Salmonella, the phoP gene product also controls the expression of non-specific acid phosphatase from the phoN gene. A central feature of the invention are microorganisms which are avirulent as a result, in whole or in part, of a mutation in phoP, but which retain their immunogenicity. These cells are suitable as components of live vaccines.

10 Claims, 2 Drawing Sheets

VACCINES CONTAINING AVIRULENT PHOP-TYPE MICROORGANISMS

REFERENCE TO GOVERNMENT GRANT

This invention was made with Government support under Grant No. AI 24533 awarded by the National Institutes of Health. The Government has certain rights in the invention.

This application is a continuation of application Ser. No. 07/331,979, filed Mar. 31, 1989.

DESCRIPTION

1. Technical Field

The invention relates to materials and methodologies for preparing vaccines and recombinant DNA expression products, and more particularly to genetically-engineered microorganisms which are useful as vaccines and as vectors for antigen delivery.

2. References Cited

Amann and Brosius (1985), Gene 40:193.
Ashcroft, M. T. et al. (1967), Lancet ii:1056–1057.
Bacon, G. A. et al. (1951), Brit. J. Exp. Pathol. 32:85–96.
Bachmann in GENETIC MAPS 1987 (S. J. O'Brien ed., Cold Spring Harbor Laboratory) pp. 178–184.
Barrett, James T., *Textbook of Immunology*: Fourth Edition, C. V. Mosby Co., St. Louis, Mo. (1983).
Birnboim, H. C. (1983), Methods Enzymol. 100:243–255.
Bochner, B. R. et al. (1983), J. Bacteriol. 143:926–933.
Brown, A., et al, (1987), 155(1): 86–92.
Brown, R. F., Stocker, B. A. D., (1987), Infec. Immun. 55(4):892–898.
Carter, P. B. and Collins, F. M. (1974), J. Exp. Med. 139:1189–1203.
Chikami, G. K. et al. (1985), Infect. Immun. 50:420–424.
Clark, R. C., Gyles, C. L., (1987), Can. J. Vet. Res., 55(1):32–38.
Clements, J. D. and Morshidy, S. (1984), Infect. Immun. 46:564–569.
Collins, F. M. (1974), 38:371–402.
Collins, F. M. et al. (1966), J. Exp. Med. 124:601–619.
Cardineau and Curtiss (1987), J. Bio. Chem. 262:3344.
Curtiss et al (1965), J. Bacteriol. 89:28.
Curtiss et al (1982) in Microbial Drug Resistance (S. Mitsuhashi, ed.) vol. 3, pp 15–27.
Curtiss, R. III and Kelly, S. M. (1987), Infect. Immun. 55:3035–3043.
Curtiss, R. III et al. (1986) in MOLECULAR MICROBIOLOGY AND IMMUNOLOGY OF *S. Mutans* (Hamada, Kiyono, Menaker, and McGhee, eds. Elsevier Publishers) pp. 173–180.
Curtiss, R. III. et al. (1988a), Vaccine 6:155–160.
Curtiss, R. III et al (1988b), in VIRULENCE MECHANISMS OF BACTERIAL PATHOGENS (Roth, J., ed., American Society for Microbiology, Washington D.C.) p.p. 311–328.
Davis, Dulbecco, Eisen, Ginsberg, and Wood, MICROBIOLOGY (Harper and Row).
DNA CLONING, Volumes I and II (D. N. Glover, ed., 1985).
Davis, R. W., Botstein, D., and Roth, J. R. ADVANCED BACTERIAL GENETICS. A MANUAL FOR GENETIC ENGINEERING. (Cold spring Harbor Laboratory, Cold Spring Harbor, N.Y., 1980).
Dougan, G., et al. (1987), Mol. Gen. Genet, 207(2-3):402–405.
Edwards, M. F., Stocker, B. A. D. (1988), J. Bacteriol. 170(9):3991–3995.
Fields, P. I. et al. (1989), Science 243:1059–1061.
Fields, P. I., Swanson, R. V. (1986), Proc. Natl. Acad. Sci. USA, 83(14):5189–5193
Formal, S. B. et al. (1981), Infect. Immun. 34:746–750.
Fukasawa, T. and Nikaido, H. (1959), Nature 184:1167–1169.
Germanier, R. and Furer, E. (1975), J. Infect. dis. 131:553–558.
Gulig, P. A. and Curtiss, R. III (1987), Infect. Immun. 55:891–901.
HANDBOOK OF EXPERIMENTAL IMMUNOLOGY, Volumes I–IV (D. M. Weir and C. C. Blackwell, eds. 1986, Blackwell Scientific Publications).
Hitchcock, P. J. and Brown, T. M. (1983), J. Bacteriol. 154:269–277.
Hoiseth, S. and Stocker, B. A. D. (1981), Nature 241:238–239.
Hone, D., et al. (1987), J. Infect. Dis., 156(1):167–174.
Kahn et al (1979), Meth. Enzymology 68:268.
Kleckner et al (1977), J. Mol. Biol. 116:125.
Kier, L. D. et al. (1979), J. Bacteriol. 138:155–161.
Laemmli, U. K. (1970), Nature 227: 680–685.
Lissner, C. R. et al. (1983), J. Immunol. 131:3006–3013.
Lennox, E. S. (1955), Virology 1:190–206.
Lugtenberg et al (1973), J. Bacteriol. 113:96.
Maniatis, Fritsch and Sambrook, MOLECULAR CLONING: A LABORATORY MANUAL (Cold Spring Harbor Laboratories, 1982).
METHODS IN ENZYMOLOGY (Academic Press, Inc.);
Manoil, C., and Beckwith, J. (1985), Proc. Natl. Acad. Sci. USA 82:8129–8133.
Maskell, D. J. et al (1987), Microb. Pathogen. 2:211–221.
McFarland, W. C. and Stocker, B. A. D. (1987), Microb. Pathogen. 3:129–141.
Miller, J. F. et al (1989), Science 243:916–922.
Miller, V. L. and Mekalanos, J. J. (1984), Proc. Natl. Acad. Sci. USA 81: 3471–3475.
Miller, EXPERIMENTS IN MOLECULAR GENETICS (1972, Cold Spring Harbor Laboratory).
Miyaka et al (1972), J. Bacteriol. 112:950.
Morris, H. A. et al. (1985), Lancet i: 1472–1474.
Mukkur, T. K. S. et al. (1987), J. Med. Microbiol. 24:11–19.
Nakayama et al (1988), Biotech. 6:693.
Neihardt, F. C. et al (1974), J. Bacteriol. 119:736–747.
NUCLEIC ACID HYBRIDIZATION (B. D. Hames and S. J. Higgins, eds., 1984).
O'Callaghan, D. et al. (1988), Infect. Immun. 56:419–423.
Ohta, M., et al. (1987), Microbiol. Immunol., 31(12):1259–1265.
OLIGONUCLEOTIDE SYNTHESIS (M. J. Gait ed. 1984).
O'Callaghan, D. et al. (1988), Infect. Immun. 56:419–423.
Perbal, A PRACTICAL GUIDE TO MOLECULAR CLONING (1984).
Robertson, J. A. et al. (1983), Infect. Immun. 41:742–750.

Sanderson and Roth in GENETIC MAPS 1987 (S. J. O'Brien, ed., Cold Spring Harbor Laboratory) pp. 155-177.

Schmeiger, H. (1972), Mol. Gen. Genet. 119:75-88.

Schneider, H. A. and Zingerm, N. D. (1956), J. Exp. Med. 103:207-223.

Stevenson, G. and Manning, P. A. (1985), FEMS Microbio. Letters 28:317-321.

Toh-E, A. et al. (1973), J. Bacteriol. 113:727-738.

Tsai, C. M. and Frasch, C. E. (1982), Anal. Biochem. 119:115-119.

VECTORS: A SURVEY OF MOLECULAR CLONING VECTORS AND THEIR USES (R. L. Rodriguez and D. T. Denhardt, eds., 1987, Butterworths);

Wilson, A. D., Stocker, B. A. D., ANNUAL MEETING OF THE AMERICAN SOCIETY FOR MICROBIOLOGY, Miami Beach, Fla., May 8-13, 1988. Abstr. Annu. Meet. Am. Soc. Microbiol. 88(0).

BACKGROUND

Previously used vaccines against infectious diseases have generally fallen into four categories: (I) specific components from the etiologic agents, including intact antigens, fragments thereof, or synthetic analogs of naturally occurring antigens or epitopes; (II) antiidiotypic antibodies, (III) the whole killed etiologic agent, or (IV) an avirulent (attenuated) derivative of the etiologic agent as a live vaccine. Attenuated vaccines have the advantage of acting like the natural infection with regard to their effect on immunity. They multiply in the host and, if immunogenic, tend to stimulate longer-lasting antibody production, to induce a cell-mediated response, and to induce antibody production and resistance at the portal of entry.

It has been possible to develop avirulent strains by the introduction of mutations into potentially pathogenic strains of the organism, which result in a lowered capacity of the mutated organism to survive in the host. The principles of the use of attenuated organisms are illustrated by reference to the Salmonella system; however, the principles are broadly applicable.

The reasons why attention has been paid to the development of avirulent strains of Salmonella are two fold. [For examples of the development of avirulent strains see Bacon et al. (1951), Curtiss and Kelly (1987), Germanier and Furer (1975), and Hoiseth and Stocker (1981)]. First, there is cumulative evidence that live attenuated strains of Salmonella are more effective than killed or subunit vaccines in inducing a protective immune response against infection by different species of Salmonella in humans and animals. [Hoiseth and Stocker (1981); Ashcroft et al. (1987), Collins (1974); Collins et al. (1966); Mukkur et al. (1987); and Robertson et al. (1983)]. Second, members of the Salmonella family with invasive properties, for example, *S. typhimurium* and *S. typhi*, after oral ingestion, enter deep tissues by attaching to, invading, and proliferating in the cells of the gut-associated lymphoid tissue (GALT; Peyer's Patches). [For example, see Carter and Collins (1974)]. Avirulent derivatives of *S. typhimurium* have been used to deliver heterologous antigens to this site as a means of stimulating a secretory as well as cellular and humoral immune responses to those antigens. [Clements and El-Morshidy (1984); Curtiss et al. (1986); Curtiss, (1988a); Curtiss, (1988b); Formal et al (1981); and Maskell et al. (1987)].

Several different strategies have been utilized to render Salmonella avirulent. These include the use of auxotrophic mutants such as aroA [Hoiseth and Stocker (1981)], asd or thy [Curtiss et al (1986)], or those defective in purine biosynthesis [McFarland and Stocker (1987); O'Callaghan et al. (1988)], mutants altered in the utilization or synthesis of carbohydrates such as galE [Germanier and Furer 1975; Fukasawa and Nikaido (1959); Stevenson and Manning (1985)]; temperature sensitive mutants [Morris et al. (1985)]; and mutants altered in global gene expression such as cya crp [Curtiss and Kelly (1987)]. These mutants have been tested and utilized with different degrees of success dependent on the host, bacterial species, and route of immunization. [Clements and El-Morshidy (1984); Curtiss et al. (1988a); Curtiss et al. (1988b); O'Callaghan et al. (1988)].

DISCLOSURE OF THE INVENTION

A surprising result has been obtained in that although phoP mutants derived from highly pathogenic strains of Salmonella were avirulent at doses which were orders of magnitude above the $LD_{50}$ dose of the wild-type parents, and although they established only limited infections of the GALT, these mutant organisms were immunogenic and offered high levels of protection against infection against the wild-type organisms. The various embodiments of the invention take advantage of the characteristics of avirulence and immunogenicity of phoP mutants in Salmonella, or phoP-type equivalent mutants in other types of microorganisms.

Accordingly, one embodiment of the invention is a vaccine for treatment of an individual for disease symptoms caused by Salmonella comprised of avirulent Salmonella which are phoP mutants which are immunogenic, and a pharmaceutically acceptable excipient.

Another embodiment of the invention is a vaccine as described above, wherein the avirulent Salmonella have at least one additional mutation which lessens the pathogenicity of wild-type Salmonella from which the avirulent Salmonella is derived.

Still another embodiment of the invention is a vaccine for treatment of an individual for disease symptoms caused by a pathogenic microorganism, wherein the vaccine is comprised of carrier Salmonella cells which are avirulent immunogenic phoP mutants, wherein the carrier cells are transformed with a recombinant expression vector encoding an immunogenic antigen from said pathogenic microorganism. Also contemplated within this embodiment are vaccines wherein the carrier Salmonella cells contain a mutation which is lethal to the cells, balanced by a recombinant gene in a vector which complements the lethal mutation to constitute a balanced lethal host-vector system.

Another embodiment of the invention is an isolated strain of Salmonella which is mutant in phoP and which contain a mutation which is lethal to the cells, balanced by a recombinant gene in a vector which complements the lethal mutation to constitute a balanced lethal host-vector system.

Still another embodiment of the invention is an isolated strain of Salmonella which is mutant in phoP and which is also delta-cya delta-crp.

Yet another embodiment of the invention is an isolated strain of Salmonella, selected from the group ATCC number 53864, ATCC number 53865, ATCC number 53866, derivatives thereof, and mutants thereof.

Other embodiments of the invention comprise methods of immunizing individuals. These include a method of immunizing an individual against a disease caused by Salmonella comprising administering to said individual a vaccine for treatment of an individual for disease symptoms caused by Salmonella comprised of avirulent Salmonella which are phoP mutants which are immunogenic, at an immunologically effective dose. The methods also include immunizing an individual against a disease caused by Salmonella comprising administering to said individual a vaccine as described above, wherein the avirulent Salmonella have at least one additional mutation which lessens the pathogenicity of wild-type Salmonella from which the avirulent Salmonella is derived at an immunologically effective dose. Also included is a method of immunizing an individual against a disease caused by Salmonella comprising administering to said individual a vaccine for treatment of an individual for disease symptoms caused by a pathogenic microorganism, wherein the vaccine is comprised of carrier Salmonella cells which are avirulent immunogenic phoP mutants, wherein the carrier cells are transformed with a recombinant expression vector encoding an immunogenic antigen from said pathogenic microorganism. Also contemplated within this embodiment are vaccines wherein the carrier Salmonella cells contain a mutation which is lethal to the cells, balanced by a recombinant gene in a vector which complements the lethal mutation to constitute a balanced lethal host-vector system. The immunization is with an immunologically effective dose.

MODES FOR CARRYING OUT THE INVENTION

A. Definitions

"Recombinant host cells", "host cells", "cells" and other such terms denoting microorganisms are used interchangeably, and refer to cells which can be, or have been, used as recipients for recombinant vectors or other transferred DNA, and include the progeny of the original cell transfected. It is understood that the progeny of a single parental cell may not necessarily be completely identical in genomic or total DNA complement as the original parent, due to accidental or deliberate mutation. Progeny of the parental cell which are sufficiently similar to the parent to be characterized by the relevant property, for example, avirulence resulting from a mutation in phoP, are included.

"Control sequence" refers to DNA sequences which are necessary to effect the expression of coding sequences to which they are ligated. Generally such control sequences include promoter and ribosome binding site. The term "control sequences" is intended to include, at a minimum, all components whose presence is necessary for expression, and may also include additional components whose presence is advantageous, for example, operators.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

A "replicon" is any genetic element, e.g., a plasmid, a chromosome, a virus, that behaves as an autonomous unit of polynucleotide replication within a cell; i.e., capable of replication under its own control.

A "vector" is a replicon in which another polynucleotide segment is attached, so as to bring about the replication and/or expression of the attached segment.

A "coding sequence" is a polynucleotide sequence which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to cDNA, and recombinant polynucleotide sequences.

The term "expression vector", as used herein, refers to a vector in which a coding sequence of interest is operably linked to control sequences.

"Gram negative bacteria" include cocci, nonenteric rods, and enteric rods. The genera of gram negative bacteria include, for example, Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema, Camphelobacter, and Fusobacterium, "Gram positive bacteria" include cocci, nonsporulating rods, and sporulating rods. The genera of gram positive bacteria include, for example, Actinomyces, Bacillus, Clostridium, Corynebacterium, Erysipelothrix, Lactobacillus, Listeria, Mycobacterium, Myxococcus, Nocardia, Staphylococcus, Streptococcus, and Streptomyces.

"Mycobacteria" are defined on the basis of their distinctive staining property, i.e., they resist decolorization with acidified organic solvents, and on the presence of long chain (approximately 60 carbons) mycolic acids.

"Facultative intracellular pathogens" include Salmonella, Yersinia, Pasteurella, Legionella, Brucella, Mycobacteria, Listeria, and Neisseria.

"Treatment" refers to the administration of the vaccine to an individual which yields a protective immune response, and includes prophylaxis and/or therapy.

A "native chromosomal gene" is one which occurs in the chromosome of a wild-type organism, for example, the gene encoding aspartic semi-aldehyde dehydrogenase (asd) in E. coli or Salmonella, the genes encoding alanine racemase, and the genes encoding D-alanyl-D-alanine ligase. Other examples of native genes are described infra.

A "recombinant gene", as used herein, is defined as an identifiable segment of polynucleotide within a larger polynucleotide molecule that is not found in association with the larger molecule in nature. The recombinant gene may be of genomic, cDNA, semisynthetic, or synthetic origin.

A "heterologous" region of a DNA construct is an identifiable segment of DNA within or attached to another DNA molecule that is not found in association with the other molecule in nature. Thus, when the heterologous region encodes a bacterial gene, the gene will usually be flanked by DNA that does not flank the bacterial gene in the genome of the source bacteria. Another example of the heterologous coding sequence is a construct where the coding sequence itself is not found in nature (e.g., synthetic sequences having codons different from the native gene). Allelic variation or naturally occurring mutational events do not give rise to a heterologous region of DNA, as used herein.

As used herein, "DAP" refers to both stereoisomers of diaminopimelic acid and its salts, i.e., both the LL- and meso-forms, unless otherwise shown by specific notation.

The gene symbols for mutant strains utilized herein are those described by Bachmann (1987), and Sanderson and Roth (1987). The symbols used for transposons, particularly Tn10, follow the convention described in Bukhari et al (1977).

An "individual" treated with a vaccine of the invention is defined herein as including all vertebrates, for example, mammals, including domestic animals and humans, various species of birds, including domestic birds, particularly those of agricultural importance. In addition, mollusks and certain other invertebrates have a primitive immune system, and are included as an "individual".

"Transformation", as used herein, refers to the insertion of an exogenous polynucleotide into a host cell, irrespective of the method used for the insertion, for example, direct uptake, electroporation, transduction, or conjugation. The exogenous polynucleotide, may be maintained as a plasmid, or alternatively, the total or part of the polynucleotide may be integrated within the host genome.

As used herein, a "phoP gene or its equivalent" refers to a gene which encodes a product which regulates the expression of other genes, including loci encoding virulence attributes (for example, facilitating colonization, invasiveness, damage to an infected individual, and survival within macrophages or cells in the immune defense network), and including a gene encoding a phosphatase, for e.g., phoN in Salmonella.

Organisms which may contain a "phoP gene or its equivalent" include all members of the family Enterobacteriaceae (e.g., *E. coli*, Salmonella, Proteus, Klebsiella, Serratia, Providencia, Citrobacter, Edwardsiella, Hafnia, and Enterobacter), members of other bacterial genera (e.g., Staphylococcus, Rhizobium, Mycobacterium, Aerobacter, Alcaligenes, and Bacillus, and several Candida species. The phoP product is a regulator of acid phosphatases [Kier et al. (1979)].

As used herein, a "pathogenic microorganism" causes symptoms of a disease associated with the pathogen.

An "avirulent microorganism" is one which has the ability to colonize and replicate in an infected individual, but which does not cause disease symptoms associated with virulent strains of the same species of microorganism. Avirulent does not mean that a microbe of that genus or species cannot ever function as a pathogen, but that the particular microbe being used is avirulent with respect to the particular animal being treated. The microbe may belong to a genus or even a species that is normally pathogenic but must belong to a strain that is avirulent. Avirulent strains are incapable of inducing a full suite of symptoms of the disease that is normally associated with its virulent pathogenic counterpart. Avirulent strains of microorganisms may be derived from virulent strains by mutation.

The term "microbe" as used herein includes bacteria, protozoa, and unicellular fungi.

A "carrier" microbe is an avirulent microbe as defined above which contains and expresses a recombinant gene encoding a protein of interest. As used herein, a "carrier microbe" is a form of a recombinant host cell.

An "antigen" refers to a molecule containing one or more epitopes that will stimulate a host's immune system to make a secretory, humoral and/or cellular antigen-specific response. The term is also used interchangeably with "immunogen."

A "hapten" is a molecule containing one or more epitopes that does not itself stimulate a host's immune system to make a secretory, humoral or cellular response.

The term "epitope" refers to a site on an antigen or hapten to which an antibody specific to that site binds. An epitope could comprise 3 amino acids in a spatial conformation which is unique to the epitope; generally, an epitope consists of at least 5 such amino acids, and more usually, consists of at least 8-10 such amino acids. The term is also used interchangeably with "antigenic determinant" or "antigenic determinant site."

An "immunological response" to a composition or vaccine is the development in the host of a cellular and/or antibody-mediated immune response to the composition or vaccine of interest. Usually, such a response consists of the subject producing antibodies, B cells, helper T cells, suppressor T cells, and/or cytotoxic T cells directed specifically to an antigen or antigens included in the composition or vaccine of interest.

By "vaccine composition" is meant an agent used to stimulate the immune system of a living organism so that protection against future harm is provided. "Immunization" refers to the process of inducing a continuing high level of antibody and/or cellular immune response in which T-lymphocytes can either kill the pathogen and/or activate other cells (e.g., phagocytes) to do so in an organism, which is directed against a pathogen or antigen to which the organism has been previously exposed. Although the phrase "immune system" can encompass responses of unicellular organisms to the presence of foreign bodies, e.g., interferon production, in this application the phrase is restricted to the anatomical features and mechanisms by which a multi-cellular organism produces antibodies against an antigenic material which invades the cells of the organism or the extracellular fluid of the organism. The antibody so produced may belong to any of the immunological classes, such as immunoglobulins A, D, E, G or M. Of particular interest are vaccines which stimulate production of immunoglobulin A (IgA) since this is the principle immunoglobulin produced by the secretory system of warm-blooded animals. Immune response to antigens is well studied and widely reported. A survey of immunology is given in Barrett, James T., *Textbook of Immunology*: Fourth Edition, C. V. Mosby Co., St. Louis, Mo. (1983).

A "vertebrate" is any member of the subphylum Vertebrata, a primary division of the phylum Chordata that includes the fishes, amphibians, reptiles, birds, and mammals, all of which are characterized by a segmented bony or cartilaginous spinal column. All vertebrates have a functional immune system and respond to antigens by producing antibodies.

The term "protein" is used herein to designate a naturally occurring polypeptide. The term "polypeptide" is used in its broadest sense, i.e., any polymer of amino acids (dipeptide or greater) linked through peptide bonds. Thus, the term "polypeptide" includes proteins, oligopeptides, protein fragments, analogs, muteins, fusion proteins and the like.

B. General Description

The practice of the present invention will employ, unless otherwise indicated, conventional techniques of cell culture, molecular biology, microbiology, recombinant DNA, and immunology, which are within the skill of the art. Such techniques are explained fully in the literature. See, e.g., Davis, R. W., Botstein, D., and Roth, J. R. ADVANCED BACTERIAL GENETICS: A MANUAL FOR GENETIC ENGINEERING. (Cold spring Harbor Laboratory, Cold Spring Harbor, N.Y., 1980), Maniatis, Fritsch and Sambrook, MOLECULAR CLONING: A LABORATORY MANUAL (1982); DNA CLONING, Volumes I and II (D. N. Glover, ed., 1985); OLIGONUCLEOTIDE SYNTHESIS (M. J. Gait ed., 1984); NUCLEIC ACID HYBRIDIZATION (B. D. Hames and S. J. Higgins, eds., 1984); B. Perbal, A PRACTICAL GUIDE TO MOLECULAR CLONING (1984); the series, METHODS IN ENZYMOLOGY (Academic Press, Inc.); VECTORS: A SURVEY OF MOLECULAR CLONING VECTORS AND THEIR USES (R. L. Rodriguez and D. T. Denhardt, eds., 1987, Butterworths); and J. H. Miller, EXPERIMENTS IN MOLECULAR GENETICS (1972, Cold Spring Harbor Laboratory), and HANDBOOK OF EXPERIMENTAL IMMUNOLOGY, Volumes I-IV (D. M. Weir and C. C. Blackwell, eds. 1986, Blackwell Scientific Publications).

All patents, patent applications, and publications mentioned herein, whether supra or infra, are hereby incorporated by reference.

A central feature of the invention are microorganisms which are avirulent as a result, in whole or in part, of a mutation in a phoP gene or its equivalent, but which retain their immunogenicity. The cells of the invention are suitable as components for live vaccines. The vaccines may be used to treat an individual to prevent a disease caused by a pathogenic strain from the family of microorganisms from which the, avirulent strains are derived, for example, Salmonella, in which case the avirulent microorganisms will be immunogenic. In other types of vaccines, the phoP type microorganisms are carrier microorganisms which contain a recombinant gene encoding a heterologous polypeptide, so that the heterologous polypeptide antigen is delivered to the colonization site in the individual treated with the vaccine.

The phoP gene and its equivalents are of a type which have "global regulation of pathogenicity", i.e., they coordinately regulate a number of genes including those that encode bacterial virulence factors. It regulates the expression of virulence genes in a fashion which may be similar to that of toxR of *Vibrio cholerae* or vir of *Bortadella pertussis*. The toxR gene is discussed in Miller and Mekalanos (1984), and Taylor et al. (1987); the vir gene is discussed in Stibitz et al. (1988). Consistent with this is the suggestion by Fields et al. (1989) that the phoP product regulates the expression of genes that allow a pathogenic microorganism to survive within macrophages, and to be insensitive to defensins, which are macrophage cationic proteins with bactericidal activity. Fields et al. (1989); Miller et al. (1989). In Salmonella, the phoP gene product also controls the expression of non-specific acid phosphatase from the phoN gene.

Some characteristics of phoP-type mutant strains are exemplified by those of the immunogenic phoP mutants of *S. typhimurium*. These avirulent mutants are able to establish an infection of the Peyer's patches of orally infected animals for a sufficient length of time to give rise to an immune response, but are very inefficient at reaching the spleens. The phoP mutants exhibit similar capability as the pathogenic parental strains to attach to and invade tissue culture cells which are indicators for virulence of the strain. The identity of these indicator cells are known by those of skill in the art; for example, pathogenic strains of Salmonella, including *S. typhimurium*, invade a variety of cells in culture, such as Henle 407, Hela, Hep-2, CHO, and MDCK cells. In addition, the Salmonella mutant strains maintain parental motility, type 1 pili, and have a lipopolysaccharide (LPS) composition similar to that of the parent strains. Moreover, the phenotype of the mutant strains is stable. Methods of determining these latter characteristics are known to those of skill in the art. It is contemplated, however, that strains carrying the phoP mutation may have their phenotypes altered by further mutations in genes other than phoP. Strains which include mutations in addition to the phoP mutation are contemplated, and are within the scope of the invention.

A further, and significant characteristic of phoP mutants results from the control of phoP over the structural gene for phosphatase, for example, non-specific acid phosphatase in Salmonella. As exemplified in Salmonella, generally, phoP-type mutants lack nonspecific acid phosphatase activity. However, this lack of phosphatase activity can be overcome by a second mutation which most likely removes the expression of the structural gene for phosphatase from the control of the phoP-type gene. Thus, mutants of phoP can be obtained which maintain their avirulence, but which are Pho+ in phenotype, and produce phosphatase. Thus, inability to produce phosphatase, per se, is not responsible for the avirulence of phoP mutants.

Strains carrying mutations in phoP or its equivalent gene, particularly desirable deletion mutations, can be generated by techniques utilizing transposons. Transposons can be added to a bacterial chromosome at many points. The characteristics of transposon insertion and deletion have been reviewed in Kleckner (1977). For example, the transposon Tn10, which confers resistance to tetracycline (and sensitivity to fusaric acid) can be used to create phoP mutants in a variety of bacterial species, including, for example, *E. coli* and a diversity of species of Salmonella, for example, *S. typhimurium, S. typhi, S. enteritis, S. dublin, S. gallinarium, S. pylorum, S. arizona*, and *S. choleraesuis*. The isolation of mutants of other organisms which contain a deletion mutation in an equivalent to a phoP gene may be achieved with transposon mutagenesis (e.g., using Tn5, Tn10, Tn916, Tn917, or other transposons known in the art) to cause the deletion in the virulent strain, and screening for a Pho− phenotype using a substrate for nonspecific/acid phosphatases (e.g., 4-bromo-3-chloro-2-indolyl phosphate, or alpha-napthyl phosphate). In the event that the microorganism contains phosphatases which are not regulated by phoP or its equivalent gene, the starting strains for transposon mutagenesis must contain mutations to inactivate these phosphatases.

One method to create a phoP mutant strain is described in the Examples, infra. Additional means are possible. In one method, insertion of $Tn_{10}$ adjacent to the phoP gene is selected in a phoP mutant of *S. typhimurium* LT-2 by propagating the transducing phage P22 HT int on a Tn10 library in the LT-2 strain X3000 (see U.S. Ser. No. 251,304) and selecting on Neidhardt medium with 12 units tetracycline/ml and 40 micrograms/ml 5-Bromo-4 Chloro-3 indolyl phosphate (BCIP) as the sole source of phosphate. Rare transductants that grow will most likely have Tn10 closely linked to the wild-type phoP+ gene. Selection of fusaric acid resistant derivatives of a number of $Tn_{10}$ transductants and plating on media with BCIP should reveal delta-phoP mutations in those cases in which the $Tn_{10}$ is close enough to phoP such that deletion of the DNA between the $Tn_{10}$ insertions can be conveniently used to move the delta-phoP mutations to other strains by standard methods (Kleckner 1977, and U.S. Ser. No. 251,304, which is owned by the herein assignee, and which is incorporated herein by reference).

Still another means of generating phoP mutations makes use of an auxotrophic mutation closely linked to the *S. typhimurium* phoP gene. The purB gene has such properties. A purB *S. typhimurium* LT-2 mutant is transduced to PurB+ using a P22 HT int lysate propagated on the Tn10 library referred to above and $Tc^r$ PhoP− PurB+ transductants are selected and identified on Neidhardt medium devoid of adenine and containing tetracycline and BCIP. The desired mutants will have Tn10 inserted into the phoP gene (i.e., phoP::Tn10). Selection for fusaric acid resistance will generate tetracycline-sensitive delta-phoP mutations.

The delta-phoP mutation isolated in *S. typhimurium* LT-2 can be transduced to other Salmonella strains by using a Tn10 insertion linked to the delta-phoP::Tn10. In either case, transductants are selected for resistance to tetracycline. If the desired highly virulent Salmonella strain to be rendered avirulent by introducing a phoP mutation is sensitive to P22, one can propagate P22 HT int on either the delta-phoP strain with the linked Tn10 or on the phoP::Tn10 mutants and use the lysate to transduce the virulent Salmonella to tetracycline resistance. The Tn10 adjacent to the delta-phoP mutation or inserted into phoP can be removed by selecting for fusaric acid resistance. In the case of the phoP::Tn10 mutant a delta-phoP mutation will be generated. If the desired highly virulent Salmonella strain to be rendered avirulent by introducing a phoP mutation is resistant to P22, one can use another transducing phage such as P1L4, which will generally only efficiently infect Salmonella strains that are rough. In this case a galE mutation can be introduced into the *S. typhimurium* LT-2 delta-phoP or phoP::Tn10 mutants either by transduction or by selection for resistance to 2-deoxygalactose (U.S. Ser. No. 251,304). Growth of galE mutants in the absence of galactose renders them rough and sensitive to P1L4 permitting the propagation of a transducing lysate. galE mutants of the virulent Salmonella recipient strain will also have to be selected using 2-deoxygalactose. Transduction of these galE recipients using P1L4 propagated on the galE delta-phoP with the linked Tn10 or the galE phoP::Tn10 strain can be achieved by plating for transductants on medium with tetracyclines and containing BCIP to identify phoP− transductants. Selection for fusaric acid resistance will eliminate Tn10 and in the case of the phoP::Tn10 mutant generate a delta-phoP mutation. The galE mutation can then be removed by P1L4 mediated transduction using P1L4 propagated on a galE+ *S. typhimurium* LT-2 strain that is rough due to a mutation in a gene other than galE. Such mutants are well known to those knowledgeable in the field (see Sanderson and Roth).

It should be obvious that recombinant DNA techniques can also be used to generate phoP mutations in various pathogenic bacteria. This can be accomplished using gene cloning and DNA hybridization technologies, restriction enzyme site mapping, generation of deletions by restriction enzyme cutting of cloned phoP sequences, and by allele replacement recombination to introduce the delta-phoP defect into a selected bacterial pathogen. Methods to accomplish this are well-known to those schooled in the art (see res. supra).

In an initial embodiment of the invention, the vaccines are for treatment of an individual for a disease caused by a pathogenic microorganism. The vaccine is comprised of an avirulent, immunogenic microorganism which contains a mutation, preferably a deletion mutation, in phoP or its equivalent gene, and a pharmaceutically suitable excipient. In a preferred embodiment, the vaccine is for treatment of a disease caused by a virulent strain of Salmonella, especially one which causes disease in animals with agricultural significance (including for example, fowl, members of the bovine, equine, ovine, porcine, or capra genuses), sporting animals and pet animals, and humans; these vaccines are comprised of avirulent phoP type mutants of Salmonella which are immunogenic, and which offer protection against the virulent strain causative of the disease.

In another embodiment, the vaccines are comprised of microorganisms with a mutation in phoP or its equivalent gene, and which also contain one or more other mutations which impart desirable characteristics to the cells in their use as vaccines, as carrier microbes, and/or as sources for the production of desired polypeptides.

An attenuated vaccine strain ideally should have a number of features. First, it should be completely avirulent and highly immunogenic. This requires a balance that is often difficult to achieve especially because of genetic diversity in the immunized population and significant differences in diet and hygiene between individuals. Second, at least in relation to avirulent Salmonella, it must retain its ability to colonize the intestine and GALT without causing disease or impairment of normal host physiology and growth. These latter attributes are particularly important when immunizing agriculturally-important animals since either temporary cessation of growth or stunting has adverse economic consequences. Third, it should have two or more attenuating mutations, preferably deletion mutations to preclude loss of the traits by reversion or gene transfer. This latter feature increases the safety of the attenuated vaccine, and is a particular consideration in human vaccines, and in vaccine strains used to immunize animals wherein the strain could be transmitted to humans via the food chain. Fourth, the attenuating phenotype should be unaffected by anything supplied in the diet or by the animal host. If the immunizing microorganism is used as a carrier microbe, the system should provide stable (and preferably high level) expression of cloned genes in the immunized individual.

Thus, in one form of this embodiment of the invention, the vaccine is comprised of a microorganism which is a facultative intracellular parasite, preferably Salmonella, which contains at least two mutations, one in the phoP gene, and one in a gene which may also act to attenuate the microorganism, and which also increases significantly the probability that the microorganism will not revert to wild-type virulence if a revision occurs in the phoP gene. These mutations may be in, for example, genes which, when mutated or deleted, cause a loss of virulence (e.g., plasmid cured strains), cause the strain to be auxotrophic, cause an alteration in the utilization or synthesis of carbohydrates, or are defective in global gene expression. An example of the latter are the cya crp mutants described in Curtiss and Kelly (1987). Contemplated as within the scope of this embodiment are microorganisms, particularly Salmonella, which contain two or more mutations of the type described above, as long as the microorganisms maintain their avirulence and immunogenicity. Examples of mutations in Salmonella which may be incorporated with the phoP mutation are shown in Table 1.

vaccines are particularly useful where local immunity is important and might be a first line of defense. The requirement that the carrier microbe be avirulent is met by the phoP mutation in the microbe. However, also contemplated as within the scope of this embodiment are microorganisms, particularly Salmonella, which have at least one additional mutation to lessen the probability of reversion of the microorganism to wild-type virulence. Examples of these types of mutations are described supra.

In the case of carrier microorganisms, it may also be desirable to genetically engineer the PhoP− type microorganisms so that they are "balanced lethals" in which non-expression of a recombinant heterologous polypeptide(s) is linked to death of the microorganism.

"Balanced lethal" mutants of this type are characterized by a lack of a functioning native chromosomal gene

TABLE 1

Mutations rendering Salmonella avirulent

| Gene | Mutant phenotype | Reference |
|---|---|---|
| pab | requirement for pABA | BACON et al., 1950, 1951 BROWN and STOCKER, 1987 |
| asp* | requirement for aspartic acid | BACON et al., 1950, 1951; KELLY AND CURTISS, unpublished |
| his* | requirement for histidine | BACON et al., 1950, 1951; FIELDS et al., 1986 |
| cys* | requirement for cystine | BACON et al., 1950, 1951 |
| pur | requirement for purines | BACON et al., 1950, 1951; MCFARLAND and STOCKER, 1987; FIELDS et al., 1986 |
| aroA | requirement for aromatic amino acids, pABA and dihydroxybenzoic acid | HOISETH and STOCKER, 1981; BOUGAN et al., 1987b |
| asd | requirement for threonine, methionine, and diaminopimelic acid | CURTISS, 1985 |
| dap | requirement for diaminopimelic acid | CLARKE and GYLES, 1987 |
| purA | requirement for adenine | BROWN and STOCKER, 1987 |
| purHD | requirement for hypoxanthine and thiamine | EDWARDS and STOCKER, 1988 |
| nadA | requirement for quinolinic acid | WILSON and STOCKER, 1988 |
| pncB | requirement for nicotinic acid or nicotinamide mononucleotide | WILSON and STOCKER, 1988 |
| ilv* | requirement for isoleucine and valine | KELLY and CURTISS (unpublished) |
| val* | requirement for valine | KELLY and CURTISS (unpublished) |
| $Str^d$ | streptomycin-dependent | REITMAN 1967 |
| galE | renders cells reversibly rough | GERMANIER and FURER, 1971, 1975; HONE et al., 1987 |
| Δ[ptsH, I, crrA] | inability to transport and phosphorylate a number of carbohydrates and to regulate cell metabolism | CURTISS and KELLY (unpublished) |
| pmi | renders cells reversibly rough | KELLY and CURTISS (unpublished) |
| Ts | decrease cell proliferation at 37° C. | OHTA et al., 1987; |
| cya | inefficient transport and use of carbohydrates and amino acids and inability to synthesize cell surface structures | CURTISS and KELLY, 1987 |
| crp | inefficient transport and use of carbohydrates and amino acids and inability to synthesize cell surface structures | CURTISS and KELLY, 1987 |

*Only some mutants of these types are avirulent and the avirulent mutants have not been investigated for immunogenicity.

In another embodiment of the invention the vaccines are comprised of microorganisms with a mutation in phoP or its equivalent gene, and the microorganisms are "carriers" which contain a recombinant gene(s) encoding a heterologous polypeptide(s) so that the expression product(s) of the recombinant gene(s) is delivered to the colonization site in the individual treated with the vaccine. The recombinant gene in the carrier microorganisms would encode an antigen of a fungal, bacterial, parasitic, or viral disease agent, or an allergen. Live encoding an enzyme which is essential for cell survival, preferably an enzyme which catalyzes a step in the biosynthesis of an essential cell wall structural component, and even more preferably a gene encoding beta-aspartic semialdehyde dehydrogenase (asd). The mutants, however, contain a first recombinant gene encoding an enzyme which is a functional replacement for the native enzyme, wherein the first recombinant gene cannot replace the defective chromosomal gene. The first recombinant gene is structurally linked to a second recombinant gene encoding a desired product. Loss of the first recombinant gene causes the cells to die, by lysis in the cases of loss of asd, when the cells are in an environment where a product due to the expression of the first recombinant gene is absent. Methods of preparing these types of "balanced lethal" mutants are disclosed in U.S. Ser. No. 251,304, filed Oct. 3, 1988, which is commonly owned by the herein assignee, and which is incorporated herein by reference. It should be pointed out that "balanced lethal" mutants which are avirulent due to a mutation in a phoP-type gene, or in phoP, would also have utility in the commercial production of desired products, and for release into the environment.

In the embodiments of the invention, the avirulent derivative(s) of a pathogenic microbe also referred to herein as a carrier bacterium can be used to deliver selected antigens to the GALT, for example to the Peyer's patches of the ileum. Some genera of bacteria, such as Salmonella, are known to home to the Peyer's patches (Carter, P. B. and F. M. Collins, J. Exp. Med. 139:1189 (1974)). S. typhimurium-E. coli hybrids have also been shown to colonize Peyer's patches in mice (Hohmann, A. W., et al, Infect. and Immun. 22:763 (1978)). If these carrier bacteria contain and express a recombinant gene from a pathogenic organism, antibodies against the antigenic gene product produced from the pathogen will be induced. With the advent of recombinant DNA techniques, it now becomes possible to develope totally unique vaccines in which specific antigens are produced, not by the etiologic agent, but by another host strain of bacteria capable of expressing the gene for that antigen. It is also possible, when antigens might cross-react with an antigen of the mammalian host and thus potentiate the induction of autoimmunity, to use recombinant DNA techniques to alter the gene so that the affecting cross-reacting antigenic determinant is not produced. Thus, recombinant DNA techniques can be employed to develop vaccines that do not have any material capable of cross-reacting with vertebrate host antigens or capable of eliciting an autoimmune state.

It is apparent that the present invention has wide applicability to the development of effective vaccines against bacterial, fungal, parasite or viral disease agents where local immunity is important and might be a first line of defense. Some examples are vaccines for the control of pneumonic plague caused by Yersinia pestis, of gonorrhea caused by Neisseria gonorrhoeae, of syphilis caused by Treponema pallidum, and of venereal diseases as well as eye infections caused by Chlamydia trachomatis. Species of Streptococci from both group A and group B, such as those species that cause sore throat or heart diseases, Neisseria meningitidis, Mycoplasma pneumoniae, Hemophilus influenza, Bordetella pertussis, Mycobacterium tuberculosis, Mycobacterium leprae, Bordetella avium, Escherichia coli, Streptococcus equi, Streptococcus pneumoniae, Brucella abortus, Pasteurella hemolytica, Vibrio cholera, Shigella species, and Legionella pneumophila are additional examples of bacteria within the scope of this invention from which genes could be obtained. Viral vaccines, such as those produced against influenza viruses, are also encompassed by this invention. Viral vaccines can also be produced against other viruses, either DNA or RNA viruses, for example from the classes Papovirus, Adenovirus, Herpesvirus, Poxvirus, Parvovirus, Reovirus, Picornavirus, Myxovirus, Paramyxovirus, or Retrovirus. Vaccines to protect against infection by pathogenic fungi, protozoa and parasites are also contemplated by this invention.

In a further embodiment when the immunogenic component of the vaccine is an allergen of the host such a vaccine may be used in an exposure regimen designed to specifically desensitize an allergic host.

In one of its embodiments, the invention can be described as a vaccine for the immunization of a vertebrate animal comprising a live avirulent derivative of a pathogenic microbe said derivative being substantially incapable of producing functional adenylate cyclase and AMP receptor protein while being capable of expressing a recombinant gene derived from an organism that is a pathogen of or that produces an allergen of said animal.

In yet another embodiment the avirulent microbes of this invention may be used as vectors for the synthesis of various host proteins. Because the avirulent microbes of this invention are able to traverse a variety of immunocompetent structures including GALT, mesenteric lymph nodes and spleen after introduction into the host, such microbes may be used to target a variety of immunoregulatory products. Accordingly, one or more genes encoding immunoregulatory proteins or peptides may be recombinantly introduced into the avirulent microbes such that when the microbes taking up residence in the appropriate immunocompetent tissue are capable of expressing the recombinant product to suppress, augment or modify the immune response in the host. Examples of immunoregulatory molecules include but are not limited to: colony stimulating factors (macrophage, granulocyte, or mixed), macrophage chemotoxin, macrophage inhibition factor, leukocyte inhibitory factors, lymphotoxins, blastogenic factor, interferon, and interleukins.

Each of the terms in these embodiments of the invention is analyzed in the following discussion.

By vaccine is meant an agent used to stimulate the immune system of a living-organism so that protection against future harm is provided. Immunization refers to the process of inducing a continuing high level of antibody and/or cellular immune response in which T-lymphocytes can either kill the pathogen and/or activate other cells (e.g., phagocytes) to do so in an organism, which is directed against a pathogen or antigen to which the organism has been previously exposed. Although the phrase "immune system" can encompass responses of uni-cellular organisms to the presence of foreign bodies, e.g., interferon production, in this application the phrase is restricted to the anatomical features and mechanisms by which a multi-cellular organism produces antibodies against an antigenic material which invades the cells of the organism or the extra-cellular fluid of the organism. The antibody so produced may belong to any of the immunological classes, such as immunoglobulins A, D, E, G or M. Of particular interest are vaccines which stimulate production of immunoglobulin A (IgA) since this is the principle immunoglobulin produced by the secretory system of warm-blooded animals, although vaccines of the invention are not limited to those which stimulate IgA production. For example, vaccines of the nature described herein are likely to produce a broad range of other immune responses in addition to IgA formation, for example, cellular and humoral immunity. Immune response to antigens is well studied and widely reported. A survey of immunology is given in Barrett, James T., Textbook of

*Immunology*: Fourth Edition, C. V. Mosby Co., St. Louis, Mo. (1983).

In one embodiment of the invention is the use of an avirulent derivative of a pathogenic microbe that homes to the GALT or BALT as a carrier of the gene product which is used for stimulating antibody response against a pathogen or allergen. Avirulent does not mean that a microbe of that genus or species can not ever function as a pathogen, but that the particular microbe being used is avirulent with respect to the particular animal being treated. The microbe may belong to a genus or even a species that is normally pathogenic but must belong to a strain that is avirulent. By pathogenic is meant capable of causing disease or impairing normal physiological functioning. Avirulent strains are incapable of inducing a full suite of symptoms of the disease that is normally associated with its virulent pathogenic counterpart. Microbes as used herein include bacteria, protozoa, and unicellular fungi.

Techniques for transferring genetic material from a first organism to a second organism which normally does not exchange genetic material with the first organism, have recently become widely available as the result of rapidly expanding recombinant DNA technology. In this application, genetic material that has been transferred from one organism into a second in such a manner that reproduction of the second organism gives rise to descendants containing the same genetic material is referred to as a recombinant gene. The term gene is being used here in its broadest sense to represent any biological unit of heredity. It is not necessary that the recombinant gene be a complete gene as present in the parent organism, which was capable of producing or regulating the production of a macromolecule, for example, a functioning polypeptide. It is only necessary that the gene be capable of serving as the template used as a guide in the production of an antigenic product. The product may be one that was not found in that exact form in the parent organism. For example, a functional gene coding for a polypeptide antigen comprising 100 amino acid residues may be transferred in part into a carrier microbe so that a peptide comprising only 75, or even 10, amino acid residues is produced by the cellular mechanism of the host cell. However, if this gene product is an antigen that will cause formation of antibodies against a similar antigen present in the parent organism, the gene is considered to be within the scope of the term gene as defined in the present invention. Alternatively, if the amino acid sequence of a particular antigen or fragment thereof is known, it is possible to chemically synthesize the DNA fragment or analog thereof by means of automated gene synthesizers or the like and introduce said DNA sequence into the appropriate expression vector. At the other end of the spectrum is a long section of DNA coding for several gene products, one or all of which can be antigenic. Thus a gene as defined and claimed here is any unit of heredity capable of producing an antigen. The gene may be of chromosomal, plasmid, or viral origin.

In order for the gene to be effective in eliciting an immune response, the gene must be expressed. Expression of a gene means that the information inherent in the structure of the gene (the sequence of DNA bases) is transformed into a physical product in the form of a RNA molecule, polypeptide or other biological molecule by the biochemical mechanisms of the cell in which the gene is located. The biological molecule so produced is called the gene product. The term gene product as used here refers to any biological product or products produced as a result of the biochemical reactions that occur under the control of a gene. The gene product may be, for example, an RNA molecule, a peptide, or a product produced under the control of an enzyme or other molecule that is the initial product of the gene, i.e., a metabolic product. For example, a gene may first control the synthesis of an RNA molecule which is translated by the action of ribosomes into an enzyme which controls the formation of glycans in the environment external to the original cell in which the gene was found. The RNA molecule, the enzyme, and the glycan are all gene products as the term is used here. Any of these as well as many other types of gene products, such as glycoproteins and polysaccharides, will act as antigens if introduced into the immune system of an animal. Protein gene products, including glycoproteins and lipoproteins, are preferred gene products for use as antigens in vaccines.

In order for a vaccine to be effective in producing antibodies, the antigenic material must be released in such a way that the antibody-producing mechanism of the vaccinated animal can come into play. Therefore the microbe carrier of the gene product must be introduced into the animal. In order to stimulate a preferred response of the GALT or BALT cells as discussed previously, introduction of the microbe or gene product directly into the gut or bronchus is preferred, such as by oral administration, gastric intubation or in the form of aerosols, although other methods of administering the vaccine, such as intravenous, intramuscular, subcutaneous injection or intramammary or intrapenial or vaginal administration, is possible.

When the avirulent microbe is used, as a carrier microbe and once the carrier microbe is present in the animal, the antigen needs to become available to the animal's immune system. This may be accomplished when the carrier microbe dies so that the antigen molecules are released. Of course, the use of "leaky" avirulent mutants that release the contents of the periplasm without lysis is also possible. Alternatively, a gene may be selected that controls the production of an antigen that will be made available by the carrier cell to the outside environment prior to the death of the cell.

The use of the avirulent strain with asd mutations and occasional loss of the Asd+ cloning vector would permit lysis of approximately 1% of the bacteria during each generation (see examples) to release the cell contents to thus stimulate an immune response against the released cell contents including any colonization and virulence antigens.

The use of pathogens to deliver antigens from other pathogens to the GALT or BALT would be inappropriate if it were not for the fact that such pathogens can be rendered avirulent while retaining ability to invade Peyer's patches or the BALT.

The organism from which the recombinant gene is derived may be any pathogen of the animal being vaccinated or may be an organism that produced an allergen or other antigen of the animal. Allergens are substances that cause allergic reaction, in this case in the animal which will be vaccinated against them. Many different materials may be allergens, such as animal dander and pollen, and the allergic reaction of individual animals will vary for any particular allergen. It is possible to induce tolerance to an allergen in an animal that normally shows an allergic response. The methods of inducing tolerance are well-known and generally comprise administering the allergen to the animal in increasing dosages. Further discussion of tolerance induction is given in the Barrett textbook previously cited. Lastly the host organism itself can serve as a source of genetic material when immunoregulatory genes are being expressed by the vectors.

Administration of a live vaccine of the type disclosed above to an animal may be by any known or standard technique. These include oral ingestion, gastric intubation, or broncho-nasal spraying. All of these methods allow the live vaccine to easily reach the GALT or BALT cells and induce antibody formation and are the preferred methods of administration. Other methods of administration, such as intravenous injection, that allow the carrier microbe to reach the animal's blood stream may be acceptable. Intravenous, intramuscular or intramammary injection are also acceptable with other embodiments of the invention, as is described later.

Since preferred methods of administration are oral ingestion, aerosol spray and gastric intubation, preferred carrier microbes are those that belong to species that home preferentially to any of the lymphoepithelial structures of the intestines or of the bronchii of the animal being vaccinated. These strains are preferred to be avirulent derivatives of enteropathogenic strains produced by genetic manipulation of enteropathogenic strains. Strains that home to Peyer's patches and thus directly stimulate production of IgA are most preferred. In animals these include specific strains of Salmonella, and Salmonella-*E. coli* hybrids that home to the Peyer's patches.

Recombinant DNA techniques are now sufficiently well known and widespread so as to be considered routine. In very general and broad terms, this method consists of transferring the genetic material, or more usually part of the genetic material, of one organism into a second organism so that the transferred genetic material becomes a permanent part of (recombines with) the genetic material of the organisms to which it is transferred. This usually consists of first obtaining a small piece of DNA from the parent organism either from a plasmid or a parent chromosome. A plasmid (also called an extrachromosomal element) is a hereditary unit that is physically separate from the chromosome of the cell. The DNA may be of any size and is often obtained by the action of a restriction endonuclease enzyme which acts to split DNA molecules at specific basepair sites. Following ligation to plasmid, phage or cosmid vectors to form recombinant molecules the recombinant molecules may be transferred into a host cell by various means such as transformation (uptake of naked DNA from the external environment, which can be artificially induced by the presence of various chemical agents, such as calcium ions). Other methods such as transduction are also suitable, wherein the recombinant DNA is packaged within a phage. Suitable transducing phages are known in the art, and include, but are not limited to transducing phages for cosmid vectors. Once the recombinant DNA is in the carrier cell, it may continue to exist as a separate piece (generally true of complete transmitted plasmids) or it may insert into the host cell chromosome and be reproduced with the chromosome during cell division.

Derivatives of avirulent microbes are also contemplated to be within the scope of this invention. By derivative is meant sexually or asexually derived progeny and mutants of the avirulent strains including single or multiple base substitutions, deletions, insertions or inversions which retain the properties of avirulence and immunogenicity.

The dosages required of the avirulent bacteria, or of the recombinant derivatives used as carrier microorganisms, will vary with the antigenicity of the bacteria or gene product, and need only be an amount sufficient to induce an immune response typical of existing vaccines. Routine experimentation will easily establish the required amount. Multiple dosages may be used, as needed, to provide the desired level of protection.

After growth and harvesting of the bacterial strains, the cells may be lyophilized, particularly if they are to be mixed in foodstuffs, or prepared in capsules. The vaccines comprised of the avirulent phoP mutant bacteria may be prepared using any excipient which is pharmaceutically acceptable for the individual being treated. For example, if the vaccine is to be administered in solid form, the cells may be coated with, and/or encapsulated in a material that is non-toxic to the inoculated individual and compatible with the bacteria. If the administration is to be in liquid form, the cells may be suspended in a suitable liquid carrier, including for example, skim milk, normal saline and/or other non-toxic salts at or near physiological concentrations, and other suitable liquid carriers known to those of skill in the art. If it is desirable, adjuvants may also be added. When the vaccine is prepared for administration via bronchial tubes, it may be prepared in a suitable buffer, and is preferably presented in the form of an aerosol.

The pharmaceutical excipient in which the vaccine is suspended or dissolved may be any solvent or solid or encapsulated in a material that is non-toxic to the inoculated animal and compatible with the carrier organism or antigenic gene product. Suitable pharmaceutical excipients include liquid carriers, such as normal saline and other non-toxic salts at or near physiological concentrations, and solid carriers not used for humans, such as talc or sucrose, also feed for farm animals. Adjuvants may be added to enhance the antigenicity if desired. When used for administering via the bronchial tubes, the vaccine is preferably presented in the form of an aerosol.

Immunization with a pathogen derived gene product can also be used in conjunction with prior immunization with the avirulent derivative of a pathogenic microorganism acting as a carrier to express the gene product specified by a recombinant gene from a pathogen. Such parenteral immunization can serve as a booster to enhance expression of the secretory immune response once the secretory immune system to that pathogen-derived gene product has been primed by immunization with the carrier microbe expressing the pathogen derived gene product to stimulate the lymphoid cells of the GALT or BALT. The enhanced response is known as a secondary, booster, or anamnestic response and results in prolonged immune protection of the host. Booster immunizations may be repeated numerous times with beneficial results.

The above disclosure generally describes the present invention. A more complete understanding can be obtained by reference to the following specific examples which are provided herein for purposes of illustration only and are not intended to be limiting unless otherwise specified.

EXAMPLES

Construction of *S. typhimurium* phoP Mutants

Highly virulent mouse-passaged *S. typhimurium* strains Chi3181 and Chi3339 were infected with a lysate of P22 HT int grown on *S. typhimurium* strain AD154 and transductants were selected on L agar plates containing tetracycline and 5-bromo 4-chloro-3-indolyl phosphate (BCIP). AD154 carries a stable insertion of the transposon Tn10 in purB that cotransduces at high frequency (90%) with phoP. Tetracycline-resistant, BCIP-negative transductants (white colonies) were streaked for isolation until they were free of P22 HT int phage. As a result of this process, two transductants which had integrated the Tn10 transposon, and which were mutants in phoP and purB were selected and named Chi3686 (derived from Chi3181) and Chi3688 (derived from Chi3339). These transductants were then infected with P22 HT int grown in *S. typhimurium* strain Chi3339 and plated on fusaric acid plates containing BCIP to select for recombinational loss of Tn10. Fusaric acid-resistant, BCIP-negative transductants were restreaked on the same medium until free of P22 HT int phage. Selected transductants were checked for absence of non-specific acid phosphatase activity, P22 sensitivity and ability to grow in minimal medium lacking adenine. Chi3687 and Chi3689 (Table 2) were two of the transductants derived from Chi3181 and Chi3339, respectively, that were able to grow in minimal medium and that did not show acid phosphatase activity as determined with the plate staining method described below.

In the above descriptions, the bacterial strains used, and the resulting phoP mutant strains are listed in Table 2. Chi3181 is the same as strain SR-11, described in Hoiser & Starker (1981); Chi 3339 is mouse passaged SL1344, described in Schneider (1956). Strains were maintained at −20° C. in 50% glycerol and at −70° C. in 1% Bacto-peptone containing 5% glycerol for short- and long-term storage, respectively. Bacteriophage P22 HT int, which is described in Schmeiger (1972), was used in the transduction studies. Transduction conditions using bacteriophage p22 HT int were as described in Davis (1980). Bacteria were grown in L broth or L agar as described in Lennox (1955). When needed, BCIP was added at a concentration of 40 micrograms/ml and tetracycline at a concentration of 12 micrograms/ml. Selection of tetracycline-sensitive, fusaric acid-resistant mutants was accomplished using the technique and media described by Bochner (1983).

Nonspecific acid phosphatase activity was determined using essentially the method of Toh-e et al. (1973) as modified by Kier et al. (1979). Briefly, solutions of the substrate were freshly prepared in 0.6M sodium acetate pH 5.5 at the following concentrations: alpha-naphthyl phosphate 5 mg/ml, tetrazotized-o-dianisidine 50 mg/ml. A 100 microliter aliquot of each substrate solution was added to 2.8 ml of 0.6% agar in 0.5M sodium acetate, pH 5.5. The soft agar containing the substrate was used as an overly for the bacterial colonies, which had been grown overnight on L agar. Colonies exhibiting nonspecific acid phosphatase activity developed an orange color within 10 min of adding the substrate.

Characterization of phoP Mutants of *S. typhimurium*

The phoP mutant strains Chi3687 and Chi3689, isolated in the above-described Example, were examined for the presence of some determinants that have been shown or suggested to be virulence attributes of *S. typhimurium*. Among these were the ability to attach to and invade Henle-407 cells, the presence of the plasmid required for virulence, motility, the presence of type 1 pili, and the LPS composition, and stability of the phenotype.

The invasion of tissue culture cells by the mutant strains Chi3687 and Chi3689 was compared to that of the parental strains, Chi3181 and Chi3339. Henle-407 cells, obtained from the ATCC were grown in 24 well plates in Eagle's minimal essential medium (MEM) supplemented with 10% (vol/vol) fetal calf serum, 5 mM glutamine, penicillin (100 units/ml) and streptomycin (100 micrograms/ml), to an approximate density of $5 \times 10^5$/well. Monolayers were infected with $10^6$ bacteria per well in Hanks balanced salt solution (HBSS) for 2 h at 37° C. in a 5% $CO_2$ atmosphere. Monolayers were then washed with 5×HBSS and lysed with phosphate buffered saline (PBS) containing 0.1% (wt/vol) sodium deoxycholate to determine adherent bacteria, or further incubated for 3 h with Eagle's MEM containing 100 micrograms/ml gentamicin to eliminate extracellular bacteria before being lysed in a similar manner. The results of the comparison are shown in Table 3, where it may be seen that both mutant strains, Chi3687 and Chi3689, were equivalent to the parental wild-type strains in their ability to attach to and invade Henle-407 cells. (I.e., the inocula recovered from tissue culture cells after 3 hours of treatment with gentamicin were essentially identical for the mutant and parent strains.)

TABLE 2

| Bacterial Strains | | |
|---|---|---|
| Strain | Genotype | Description |
| Chi3181 | Prototroph | SR-11 isolated from Peyer's patch of an infected mouse [Schneider et al. (1956)] |
| Chi3339 | rpsL hisG | Mouse-passaged SL1344 [Hoiseth and Stocker (1981)] |
| Chi3686 | phoP12 purB::Tn10 | P22 HT int(AD154) = Chi3181 |
| Chi3687 Tet | phoP12 | P22 HT int(Chi3339) = Chi3686 with FA |
| Chi3688 | rpsL hisG phoP12 purB::Tn10 | P22 HT int(AD154) = Chi3339 |
| Chi3689 Tet | rpsL hisG phoP12 | P22 HT int(Chi3339) = Chi3688 with FA |
| AD154 | phoP12 purB::Tn10 | LT-2; From E.I. Eisenstadt |

TABLE 3

Penetration of Henle 407 Cells by *S. tryphimurium*

| Strain | Relevant Genotype | % Adherence[a] | % Invasion[b] |
|---|---|---|---|
| Chi3181 | wild-type | 11.5 ± 5.5 | 16.1 ± 7.2 |
| Chi3687 | phoP | 10.4 ± 4.8 | 15.2 ± 6.8 |
| Chi3339 | wild-type | 15.3 ± 8.3 | 19.3 ± 8.7 |
| Chi3689 | phoP | 13.6 ± 7.7 | 17.5 ± 7.8 |

[a]Percentage of total inoculum recovered after infection. Values represent the mean ± SD for three determinations.
[b]Percentage of total inoculum recovered after infection and treatment with gentamicin. Values represent the mean ± SD for three determinations.

In the above studies, the bacterial strains were grown in L broth standing overnight at 37° C., diluted in prewarmed L broth and grown with shaking until cultures reached an $OD_{600}$ of 0.7–0.9. Minimal media were prepared as described in Neidhardt (1974).

The presence or absence of the virulence plasmid was determined using the method of Birnboim (1983). The results of the analysis (data not shown) indicated that both mutant strains, as well as the parent strains, contained the 100 kb virulence plasmid. This plasmid has been shown to be essential for virulence of *S. typhimurium* in mice. See, for example, Gulig and Curtiss (1987).

Motility was determined with motility media from Difco (Difco Laboratories, Detroit, Mich.). The presence or absence of type I pili was determined by hemagglutination using freshly drawn guinea pig red blood cells at a concentration of 3% (v/v) in phosphate buffered saline. Analysis of the motility and pili showed that the phoP mutants were motile, and expressed type I pili (data not shown).

The LPS composition of the phoP mutants was compared to that of a parental strain, utilizing essentially the method of Hitchcock and Brown (1983). The analysis was on polyacrylamide gels in the presence of sodium dodecyl sulfate (SDS) prepared according to Laemmli (1970). After electrophoresis, the gels were stained by the method of Tsai and Frasch (1982). An examination of the stained gels showed that the LPS composition of the mutant strains, Chi3687 and Chi3689, were similar to that of the parent strains, Chi3181 and Chi3339 (data not shown).

The stability of the phenotype of the mutant strains was determined by plating cells in minimal medium supplemented with BCIP as the only phosphate source. Under this condition the frequency or reversion to Pho+ was $8 \times 10^{-8}$ for Chi3687, and $3 \times 10^{-9}$ for Chi3689.

Virulence of phoP Mutants in Mice

The virulence of phoP mutant strains Chi3687 and Chi3689 were compared to that of the parental strains Chi3181 and Chi3339 by inoculating BALB/c mice with different doses of the strains both intraperitoneally (i.p.) and per orally (p.o.), and by examining the inoculated animals for signs of illness.

Eight- to ten-week-old female BALB/c mice (Sasco, Inc., St. Louis, Mo.) were used. Inoculations given p.o. were by the following procedure. The mice were starved for food and water for 4 hours, fed 50 microliters of 10% (wt/vol) sodium bicarbonate followed by 20 microliters of the appropriate bacterial suspension in buffered saline containing 0.1% (wt/vol) gelatin (BSG). Food and water were returned 30 min after inoculation. Inoculations given i.p. were accomplished by injecting mice with 100 microliters of the appropriate mutant or wild-type bacterial suspension in BSG using a 26-gauge needle. In these studies, the bacterial count was determined using MacConkey agar.

The results of the infectivity studies for the bacteria administered by the p.o. and i.p. routes are shown in Tables 4 and 5, respectively. Mice inoculated p.o. with Chi3687 or Chi3689 survived the oral challenge with a number of organisms that represented $10^4$ times the oral $LD_{50}$ dose of the wild-type parent strains (Table 4). Survivors did not show any signs of disease and remained healthy for at least 30 days after challenge. Similar results were obtained when the mice received the phoP mutant strains by the i.p. route (Table 5).

TABLE 4

Virulence of phoP Mutants of *S. typhimurium* After Peroral Inoculation

| Strain | Relevant Genotype | Dose (CFU) | Survivors/Total[a] | Appearance[b] |
|---|---|---|---|---|
| Chi3181[c] | wild-type | $1 \times 10^5$ | 2/5 | Scruffy |
| Chi3687 | phoP | $2 \times 10^8$ | 5/5 | Healthy |
|  |  | $2 \times 10^9$ | 18/18 | Healthy |
| Chi3339[c] | wild-type | $2 \times 10^5$ | 1/5 | Scruffy |
| Chi3689 | phoP | $2 \times 10^8$ | 5/5 | Healthy |
|  |  | $2 \times 10^9$ | 5/5 | Healthy |

[a]Survivors 30 days after challenge.
[b]Healthy: no signs of disease; scruffy; noticeably ill.
[c]p.o. $LD_{50}$ for Chi3181 ($3 \times 10^5$ CFU) and Chi3339 ($6 \times 10^4$) have been previously determined [Gulig and Curtiss (1987)].

TABLE 5

Virulence of phoP Mutants After Intraperitoneal Inoculation

| Strain | Relevant Genotype | Dose (CFU) | Survivors/Total[a] | Appearance[b] |
|---|---|---|---|---|
| Chi3181[c] | wild-type | $2 \times 10^2$ | 0/5 |  |
| Chi3687 | phoP | $2 \times 10^4$ | 5/5 | Healthy |
|  |  | $2 \times 10^5$ | 5/5 | Healthy |
|  |  | $2 \times 10^6$ | 5/5 | Healthy |
| Chi3339[c] | wild-type | $2 \times 10^2$ | 0/5 |  |
| Chi3689 | phoP | $2 \times 10^4$ | 5/5 | Healthy |
|  |  | $2 \times 10^5$ | 5/5 | Healthy |
|  |  | $2 \times 10^6$ | 5/5 | Healthy |

[a]Survivors 30 days after inoculation.
[b]Healthy: no signs of disease; scruffy; noticeably ill.
[c]i.p. $LD_{50}$ for Chi3181 (<50 CFU) and Chi3339 (<50 CFU) have been previously determined [Gulig and Curtiss (1987)].

Tissue Distribution of phoP Mutants in Mice

The tissue distribution of mice infected orally with either the phoP mutant Chi3687, or of the wild-type parent Chi3181, was examined.

Figure 1:
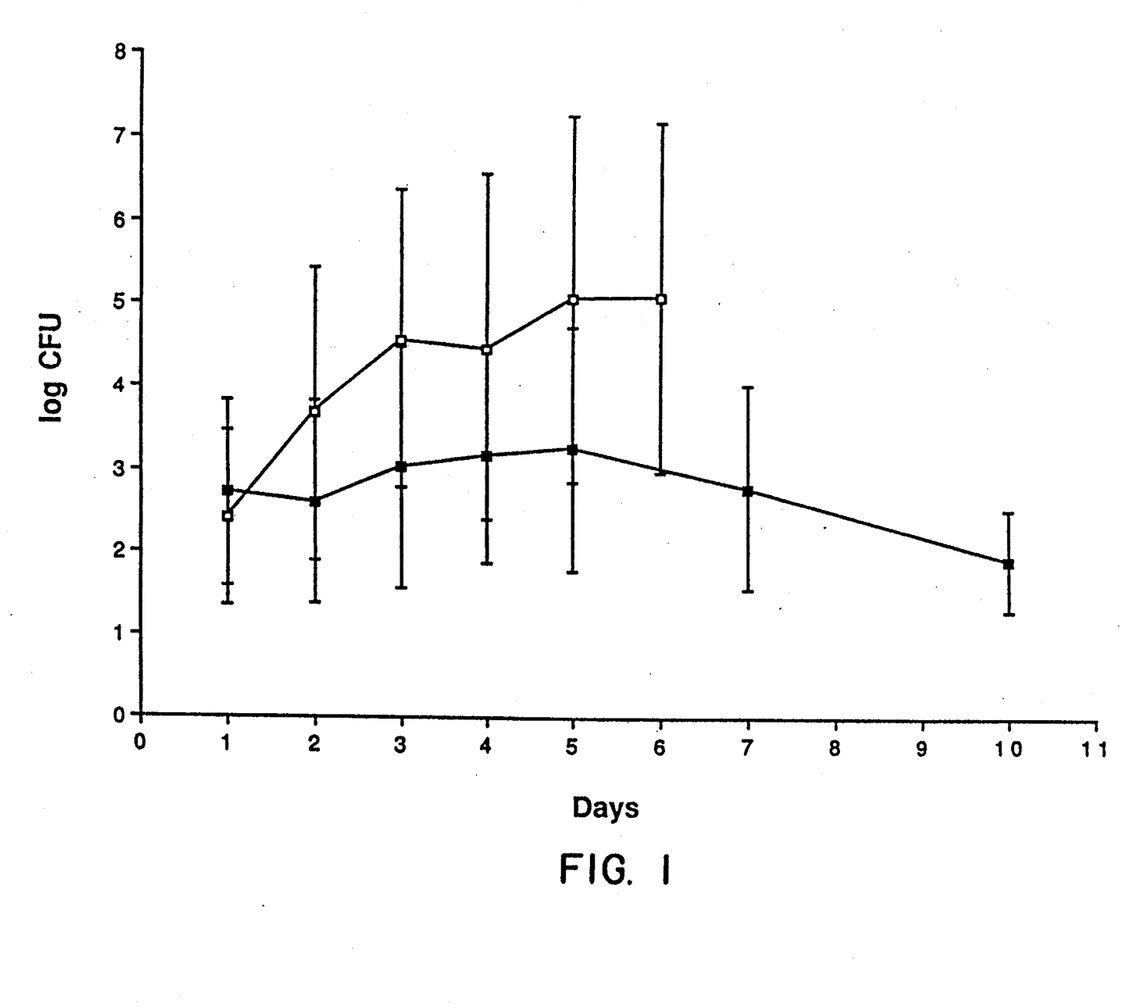
FIG. 1 shows the CFU obtained from the Peyer's patches of inoculated mice after inoculation with the Chi3687 phoP strain, and after inoculation with the Chi3181 wild-type strain.

BALB/c female mice were infected orally with approximately $10^9$ cells of either Chi3687 or Chi3181, using the procedure described in the virulence studies, supra, and the distribution of the organisms was monitored for several days. The mice were euthanized by $CO_2$ asphyxiation, the spleens were aseptically removed and homogenized with a tissue homogenizer (Brinkman instruments). Peyer's patches were excised from the small intestine, washed in BSG to remove loosely attached bacteria, and homogenized using the same homogenizer. Appropriate dilutions of the suspensions ill BSG were plated on MacConkey agar to determine the bacterial counts. The results of the studies on the colonization of Peyer's patches by the strains after the inoculation are shown in FIG. 1. In FIG. 1, the CFU obtained from the Peyer's patches after inoculation with the Chi3687 phoP strain, and after inoculation with the Chi3181 wild-type strain, are shown by the closed squares and open squares, respectively. Each time point represents the geometric mean CFU of 3 mice, and the vertical bars denote standard deviations. Mice inoculated with Chi3181 died 8 days after challenge. It is evident from FIG. 1 that phoP strain Chi3687 was able to establish an infection, albeit limited, of the Peyer's patches of the challenged mice. The numbers of the phoP mutant recovered from the Peyer's were substantially lower than those of the wild-type parental strain. By day 15 after inoculation no organisms were isolated from the Peyer's patches of mice inoculated with Chi3687.

Figure 2:
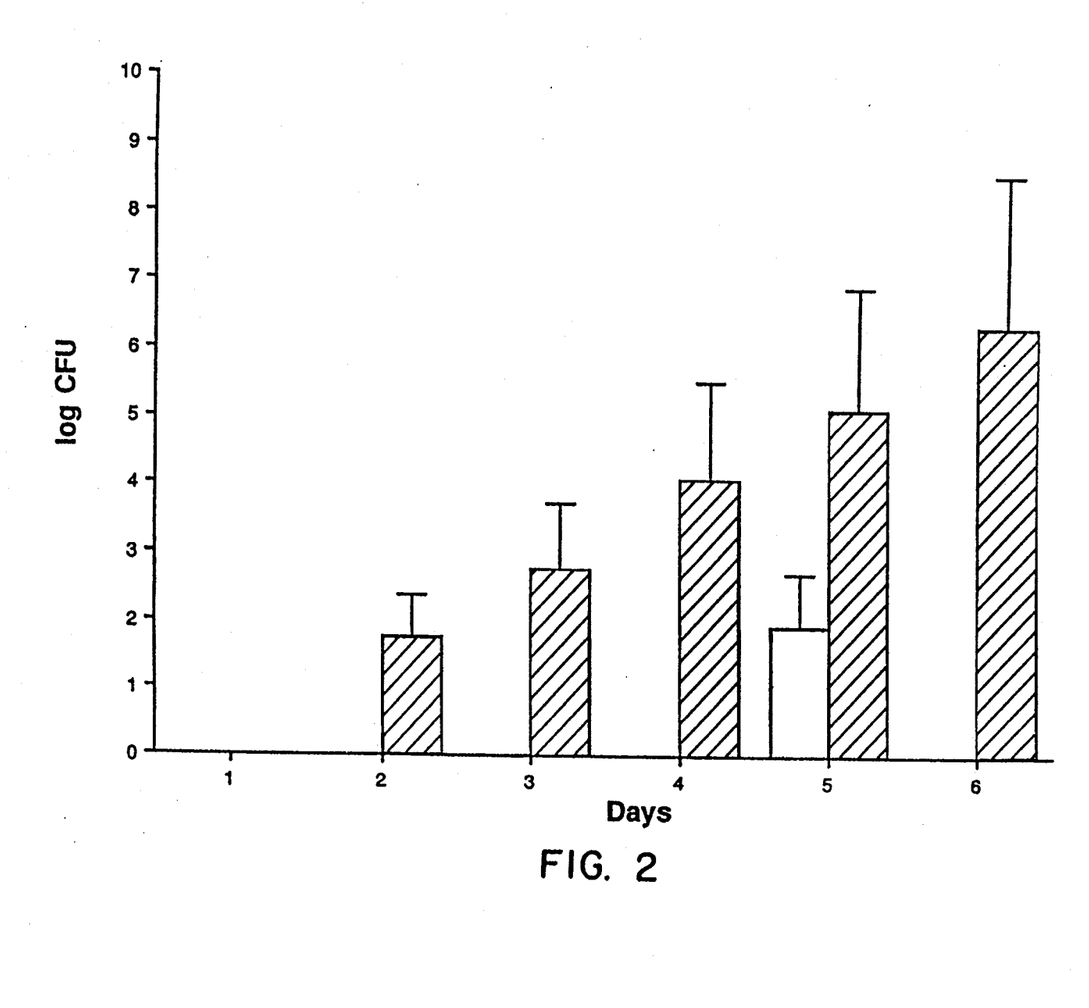
FIG. 2 shows the CFU obtained from the spleens of inoculated mice after inoculation with the Chi3687 phoP strain, and after inoculation with the Chi3181 wild-type strain.

The results on the recovery of Chi3687 and Chi3181 obtained from the spleens of the inoculated mice are shown in FIG. 2. The CFU obtained from the spleens of the mice inoculated with Chi3687 and Chi3181 are indicated by the open bar and the closed bars, respectively. Each wide bar represents the geometric mean CFU of 3 mice, and the vertical thin bars denote standard deviations. As can be seen in FIG. 2, very low numbers of Chi3687 were isolated from spleens of infected mice; organisms were recovered on day 5 after challenge from only 3 of the five infected animals observed. Moreover, Chi3687 could not be detected in the spleen 7 days after oral inoculation. Splenomegaly was absent in all of the Chi3687-infected animals examined. This low level of infectivity is in sharp contrast to the high number of wild-type (Chi3181) cells recovered from the spleens of infected animals throughout the time course of the study.

Protection of Mice Inoculated with phoP Mutants of *S. typhimurium*

BALB/c female mice were inoculated with the phoP mutant strain, Chi3687, using either the p.o. or i.p. techniques described supra. The immunization was either p.o. with approximately $10^8$ or $10^9$ CFU of the phoP mutant strain, or i.p. with approximately $10^5$ or $10^6$ CFU of the strain. Thirty days subsequent to the inoculation, the mice were challenged with the wild-type parent strain, Chi3181. The amount of wild-type organisms used in the challenge was dependent upon the route of administration, and represented $10^3$ to $10^4$ times the $LD_{50}$ for the wild-type strain.

The results of the protection of mice using the peroral route for administration and challenge is shown in Table 6. All mice survived challenge with $10^3$ $LD_{50}$ doses of Chi3181, regardless of the immunization dose. When challenged with a dose of $10^4$ $LD_{50}$ of the virulent strain, 4 of 5 mice immunized with $10^8$ CFUs of Chi3687, and 9 of 10 mice immunized with $10^9$ CFUs of this strain, survived the infection. In all cases survivors to the challenge remained healthy.

TABLE 6

Protection of Mice Against Peroral Challenge with
*S. typhimurium* SR-11 30 Days After Peroral
Immunization with *S. typhimurium* SR-11 phoP Mutants

| Immunizing Strain and Dose (CFU) | Challenge Strain and Dose (CFU) | Survivors/Total[a] | Appearance[b] |
|---|---|---|---|
| Chi3687 2 × $10^8$ | Chi3181 2 × $10^8$ | 5/5 | Healthy |
|  | Chi3181 2 × $10^9$ | 4/5 | Healthy |
| Chi3687 2 × $10^9$ | Chi3181 2 × $10^8$ | 5/5 | Healthy |
|  | Chi3181 2 × $10^9$ | 9/10 | Healthy |

[a]Survivors 30 days after challenge.
[b]Healthy: no signs of disease.

The results of the protection of mice using the i.p. route for administration and challenge is shown in Table 7. Mice immunized with $10^5$ or $10^6$ CFUs of Chi3687 resisted challenge with either $10^2$ or $10^4$ CFU of Chi3181, the latter dose being $10^4$ times the $LD_{50}$ for Chi3181 in unimmunized mice. All survivors remained healthy 30 days after challenge.

TABLE 7

Protection of Mice Against Intraperitoneal Challenge with
*S. typhimurium* SR-11 30 Days After Intraperitoneal
Immunization with *S. typhimurium* SR-11 phoP Mutants

| Immunizing Strain and Dose (CFU) | Challenge Strain and Dose (CFU) | Survivors/Total[a] | Appearance[b] |
|---|---|---|---|
| Chi3687 2 × $10^6$ | Chi3181 2 × $10^2$ | 3/3 | Healthy |
|  | Chi3181 2 × $10^4$ | 3/3 | Healthy |
| Chi3687 2 × $10^5$ | Chi3181 2 × $10^2$ | 3/3 | Healthy |
|  | Chi3181 2 × $10^4$ | 3/3 | Healthy |

[a]Survivors 30 days after challenge.
[b]Healthy: no signs of disease.

Delayed Type Hypersensitivity Responses of Mice Inoculated with PhoP Mutants of *S. typhimurium*

Delayed type hypersensitivity (DTH) is an indicator of the ability of an agent to induce a cell mediated response. In order to examine the DTH response to phoP mutants, mice were inoculated perorally with $10^9$ CFU of Chi3687, and the DTH responses measured 30 days later. The test was carried out in immunized and control animals, by injecting 20 micrograms of protein from whole cell lysates of *S. typhimurium* in 50 microliters of PBS into the right hind footpad of BALB/c mice. The same volume of PBS was injected into the contralateral footpad. Swelling was measured 2 days after inoculation with a digimatic caliper (Mitutoyo, Japan). The results are expressed as percent increase swelling of the inoculated footpad over the contralateral PBS-injected control.

In order to prepare a whole cell lysate of *S. typhimurium*, SR-11 was grown in L broth to an $OD_{600}$ of 0.6, the cells were washed twice with PBS and collected by centrifugation, and the cell pellet suspended in the same buffer. The bacterial cells were then lysed using 0.1 mm glass beads in a cell disruptor (B. Braun, Melsungen AG, West Germany) and cell debris removed by centrifugation at 10,000 g for 10 min.

The results of the DTH study are shown in Table 8. Mice orally immunized with Chi3687, a phoP derivative of *S. typhimurium*, showed significantly higher foot-pad swelling than control animals ($P<0.02$) in response to injection with whole cell lysates of *S. typhimurium*.

TABLE 8

DTH Responses of Mice 30 Days After
Peroral Immunization With 2 × $10^9$ CFU
of *S. typhimurium* SR-11 phoP Mutant

| Immunizing Strain | DTH Response[a] |
|---|---|
| none | 8.8 ± 4.8 |
| Chi3687 | 31.6 ± 6.6 |

[a]Responses are expressed as percent increase of swelling of the tested footpad over the contralateral control (PBS injected) footpad two days after injection of antigen. The values represent the mean and standard deviation of 5 mice. The differences between immunized and not immunized animals were statistically significant ($P < 0.02$).

Avirulence of Pho+ Revertants of phoP Mutants

Three revertants to Pho+ of both Chi3687 and Chi3689 were tested for virulence by i.p. inoculation of $10^5$ CFU of each mutant. The 6 Pho+ revertants maintained the avirulence of the strains from which they were derived. This demonstrates that the absence of phosphatase in a phoP mutant is not responsible for avirulence, and that the phoP gene product must regulate one or more other genes necessary for wild-type virulence.

Defining Genes Controlled by the phoP Gene

Identification of important virulence determinants (i.e., genes) controlled by the phoP gene product can be achieved in one of several ways. It is likely that some, or possibly all such virulence determinants specify products that are located on the bacterial cell surface or in the periplasmic space. The transposon TnPhoA [Manoil & Beckwith(1984)], which contains the structural gene for alkaline phosphatase (AP), is uniquely suited to identify these genes. AP activity can only be expressed when the enzyme is transported across the bacterial cytoplasmic membrane to the periplasm or to the cell surface. Since the AP in TnphoA has been truncated to delete the nucleotide sequence specifying the signal sequence, AP activity can only be expressed when the TnphoA inserts into a bacterial gene for a periplasmic or cell surface protein to cause formation of a protein fusion of the TnphoA-specified AP with the signal sequence for the periplasmic or cell surface protein. In this case, AP will be transported across the cytoplasmic membrane and can be detected by imparting a blue color to colonies growing on a medium containing the chromogenic AP substrate BCIP.

In order to identify a virulence determinant as described supra, a TnphoA library is made in a wild type virulent strain of *S. typhimurium*, for example, Chi3339 (See Table 2), by infecting the strain with a suitable TnphoA transposition vector. [Manoil and Beckwith (1984)]. Since TnphoA insertion into the chromosome or the virulence plasmid in Chi3339 confers kanomycin resistance, the infection mixtures are plated on an agar medium containing kanomycin and XP. After overnight incubation, all blue colonies are picked and purified. A mixture of cells from all such blue colonies constitutes a TnphoA library which should have insertions in all genes specifying periplasmic and cell surface proteins. A P22 HT int transducing lysate is made on this library, and is used to transduce a *S. typhimurium* phoP mutant, such as Chi3689 (See Table 2). Kanomycin resistant transductants are plated on agar medium containing BCIP. Most transductant colonies will be blue; however, those with TnphoA insertions into a gene whose expression is dependent on the wild-type phoP gene product will be white. The white colonies can be picked and purified. Proof that cells in these colonies have insertions in a gene regulated by phoP is obtained by transducing these mutants to phoP+, which should now permit formation of blue colonies on media containing BCIP. Standard methods of gene cloning, DNA hybridization, and screening of *S. typhimurium* libraries followed by subcloning, in vitro coupled transcription and translation, and ultimately DNA sequencing is used to fully characterize the phoP regulated virulence gene and its product. Other studies with animals and cells in culture can be used to elucidate the mechanisms by which each such phoP regulated virulence gene product influences pathogenicity and how these gene products might be used in the development of vaccines.

Deposits of Strains

The following listed materials are on deposit under the terms of the Budapest Treaty, with the American Type Culture Collection, 12301 Parklawn Drive, Rockville, Md. The accession number indicated was assigned after successful viability testing, and the requisite fees were paid. Access to said cultures will be available during pendency of the patent application to one determined by the Commissioner to be entitled thereto under 37 CFR 1.14 and 35 USC 122. All restriction on availability of said cultures to the public will be irrevocably removed upon the granting of a patent based upon the application. Moreover, the designated deposits will be maintained for a period of thirty (30) years from the date of deposit, or for five (5) years after the last request for the deposit; or for the enforceable life of the U.S. patent, whichever is longer. Should a culture become nonviable or be inadvertently destroyed, or, in the case of plasmid-containing strains, loose its plasmid, it will be replaced with a viable culture(s) of the same taxonomic description. The deposited materials mentioned herein are intended for convenience only, and are not required to practice the present invention in view of the description herein, and in addition, these materials are incorporated herein by reference.

| Strain | Deposit Date | ATCC No. |
|---|---|---|
| Chi3687 phoP12 | Feb. 14, 1989 | 53,864 |
| Chi3688 phoP12 purB1734:: Tn10 rpsL his6 phoP12 | Feb. 14, 1989 | 53,865 |
| Chi3689 rpsL his6 phoP12 | Feb. 14, 1989 | 53,866 |

Industrial Applicability

Effective immunity with avirulent strains, particularly avirulent Salmonella strains, requires that the avirulent microorganism persist in the, gut-associated lymphoid tissue (GALT or Peyer's patches) of the immunized individual for a period of time. The phoP mutant strains of Salmonella which are derived from highly virulent strains have this capacity, as reflected in their immunogenicity. Thus, they are commercially useful in the production of vaccines. In addition, the cells of the invention can be used as sources of a deletion mutation in phoP, which by transposon mutagenesis can be transferred to other strains which when avirulent, provide desirable vaccines.

The production of a great diversity of commercially valuable by-products synthesized by genetically-engineered microorganisms has been achieved in the biotechnology industry. Stable maintenance of the genetically engineered microorganisms under fermenter growth conditions would be facilitated by the use of the cells of the invention, such as those containing in addition to the mutation in phoP or its equivalent gene, delta-asd mutations and polynucleotide inserts into the same cell which carry an asd+ gene as a selectable marker. The PhoP− phenotype increases the safety of working with the microorganisms, and the only cells which can grow and express proteins are those which encode the desired antigen. Thus, the yield of the desired product is increased under relatively safe conditions.

We claim:

1. A vaccine for immunizing an individual against disease symptoms caused by Salmonella, said vaccine being comprised of avirulent Salmonella which contain a mutation in the phoP gone, wherein said avirulent Salmonella are unable to cause Salmonella-based disease symptoms and able to colonize in lymphoid tissue for a sufficient time to induce antibody and cellular immunity, and wherein said avirulent Salmonella retain the properties of avirulence and immunogenicity of a Salmonella strain selected from the group consisting of ATCC number 53864, ATCC number 53865, and ATCC number 53866.

2. The vaccine of claim 1, wherein the avirulent Salmonella are admixed with a pharmaceutically acceptable excipient.

3. A vaccine for immunizing an individual against disease caused by a pathogenic microorganism, wherein said vaccine is comprised of carrier Salmonella cells which contain a mutation in the phoP gene which renders said carrier Salmonella cells avirulent and immunogenic, wherein said carrier Salmonella cells are transformed with a recombinant expression vector encoding an immunogenic antigen from said pathogenic microorganism, and wherein said carrier Salmonella are unable to cause Salmonella-based disease symptoms and able to colonize in lymphoid tissue for a sufficient time to induce antibody and cellular immunity, and wherein said carrier Salmonella retain the properties of avirulence and immunogenicity of a Salmonella strain selected from the group consisting of ATCC number 53864, ATCC number 53865, and ATCC number 53866.

4. The vaccine of claim 3, wherein the carrier Salmonella cells are admixed with a pharmaceutically acceptable excipient.

5. A method of immunizing an individual against a disease caused by Salmonella comprising administering to said individual the vaccine of claim 1, at an immunologically effective dose.

6. A method of immunizing an individual against a disease caused by Salmonella comprising administering to said individual the vaccine of claim 2, at an immunologically effective dose.

7. A method of immunizing an individual for disease symptoms caused by a pathogenic microorganism, comprising administering to said individual the vaccine of claim 3 at an immunologically effective dose.

8. A method of immunizing an individual for disease symptoms caused by a pathogenic microorganism, comprising administering to said individual the vaccine of claim 4 at an immunologically effective dose.

9. A method of making a vaccine which comprises admixing (1) an immunologically effective dose of avirulent Salmonella which contain a mutation in the phoP gene wherein said avirulent Salmonella are unable to cause Salmonella-based disease symptoms and able to colonize in lymphoid tissue for a sufficient time to induce antibody and cellular immunity, and wherein said avirulent Salmonella retain the properties of avirulence and immunogenicity of a Salmonella strain selected from the group consisting of ATCC number 53864, ATCC number 53865, and ATCC number 53866 with (2) a pharmaceutically acceptable carrier.

10. A method of making a vaccine which comprises admixing (1) an immunologically effective dose of carrier Salmonella cells which are avirulent and immunogenic wherein said carrier Salmonella cells contain a mutation in the phoP gene, wherein said carrier Salmonella cells are transformed with a recombinant expression vector encoding an immunogenic antigen from a pathogenic microorganism, and wherein said carrier Salmonella are unable to cause Salmonella-based disease symptoms and able to colonize in lymphoid tissue for a sufficient time to induce antibody and cellular immunity, and wherein said carrier Salmonella retain the properties of avirulence and immunogenicity of a Salmonella strain selected from the group consisting of ATCC number 53864, ATCC number 53865, and ATCC number 53866 with (2) a pharmaceutically acceptable carrier.

* * * * *